US012649061B2

(12) United States Patent

Wasserman et al.

(10) Patent No.: US 12,649,061 B2
(45) Date of Patent: Jun. 9, 2026

(54) REDUCING ELECTROSENSATION DURING APPLICATION OF ALTERNATING ELECTRIC FIELDS BY ENSURING THAT SUCCESSIVE INCREASES IN AMPLITUDE OCCUR DURING OPPOSITE PHASES OF AN AC WAVEFORM

(71) Applicant: Novocure GmbH, Root (CH)

(72) Inventors: Yoram Wasserman, Haifa (IL); Mor Ben-Tov Kuperberg, Haifa (IL); Michael Shtotland, Haifa (IL)

(73) Assignee: Novocure GmbH, Baar (CH)

( * ) Notice: Subject to any disclaimer, the term of this patent is extended or adjusted under 35 U.S.C. 154(b) by 350 days.

(21) Appl. No.: 18/398,533

(22) Filed: Dec. 28, 2023

(65) Prior Publication Data

US 2024/0216685 A1      Jul. 4, 2024

Related U.S. Application Data

(60) Provisional application No. 63/436,034, filed on Dec. 29, 2022.

(51) Int. Cl.
*A61N 1/36* (2006.01)
*A61N 1/40* (2006.01)
(52) U.S. Cl.
CPC ................................ *A61N 1/36034* (2017.08)
(58) Field of Classification Search
CPC .................................................. A61N 1/36034
See application file for complete search history.

(56) References Cited

U.S. PATENT DOCUMENTS

| | | | |
|---|---|---|---|
| 6,868,289 | B2 | 3/2005 | Palti |
| 7,016,725 | B2 | 3/2006 | Palti |
| 7,089,054 | B2 | 8/2006 | Palti |
| 7,136,699 | B2 | 11/2006 | Palti |
| 7,333,852 | B2 | 2/2008 | Palti |
| 7,467,011 | B2 | 12/2008 | Palti |
| 7,519,420 | B2 | 4/2009 | Palti |
| 7,565,205 | B2 | 7/2009 | Palti |
| 7,565,206 | B2 | 7/2009 | Palti |
| 7,599,745 | B2 | 10/2009 | Palti |

(Continued)

FOREIGN PATENT DOCUMENTS

CN          114177528 A          3/2022

OTHER PUBLICATIONS

International Search Report and Written Opinion issued in application PCT/IB2023/063298 dated Mar. 22, 2024.

*Primary Examiner* — Mallika D Fairchild
*Assistant Examiner* — Thien Jason Tran
(74) *Attorney, Agent, or Firm* — Potomac Law Group, PLLC

(57) ABSTRACT

When transducer arrays (i.e., arrays of electrode elements) are used to apply alternating electric fields to a subject's body, the subject may experience electrosensation, particularly during portions of the waveform where the amplitude of the AC voltage is ramping up. This electrosensation can be ameliorated by synchronizing the step-to-step transitions in amplitude with the AC signal so that when a given step-to-step transition occurs while the AC signal has a given polarity, the very next step-to-step transitions will occur while the AC signal has the opposite polarity.

4 Claims, 5 Drawing Sheets

(56) References Cited

U.S. PATENT DOCUMENTS

| | | |
|---|---|---|
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,440,068 B2 | 9/2016 | Palti et al. |
| 9,655,669 B2 | 5/2017 | Palti et al. |
| 9,750,934 B2 | 9/2017 | Palti et al. |
| 9,910,453 B2 | 3/2018 | Wasserman et al. |
| 10,188,851 B2 | 1/2019 | Wenger et al. |
| 10,441,776 B2 | 10/2019 | Kirson et al. |
| 10,779,875 B2 | 9/2020 | Palti et al. |
| 10,967,167 B2 | 4/2021 | Hagemann et al. |
| 11,103,698 B2 | 8/2021 | Chang et al. |
| 11,191,956 B2 | 12/2021 | Giladi et al. |
| 11,395,916 B2 | 7/2022 | Wasserman et al. |
| 2004/0176804 A1 | 9/2004 | Palti |
| 2005/0209642 A1 | 9/2005 | Palti |
| 2006/0167499 A1 | 7/2006 | Palti |
| 2006/0276858 A1 | 12/2006 | Palti |
| 2007/0225766 A1 | 9/2007 | Palti |
| 2007/0239213 A1 | 10/2007 | Palti |
| 2008/0004675 A1 | 1/2008 | King et al. |
| 2009/0076366 A1 | 3/2009 | Palti |
| 2010/0324547 A1 | 12/2010 | Palti |
| 2012/0029419 A1 | 2/2012 | Palti |
| 2012/0283726 A1 | 11/2012 | Palti |
| 2014/0330268 A1 | 11/2014 | Palti et al. |
| 2015/0328461 A1 | 11/2015 | Charlesworth et al. |
| 2017/0120041 A1 | 5/2017 | Wenger et al. |
| 2017/0215939 A1 | 8/2017 | Palti et al. |
| 2017/0281934 A1 | 10/2017 | Giladi et al. |
| 2018/0001075 A1 | 1/2018 | Kirson et al. |
| 2018/0001078 A1 | 1/2018 | Kirson et al. |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2018/0280687 A1 | 10/2018 | Carter et al. |
| 2019/0117956 A1 | 4/2019 | Wenger et al. |
| 2019/0117963 A1 | 4/2019 | Travers et al. |
| 2019/0117970 A1 | 4/2019 | Schmidt et al. |
| 2019/0224474 A1 | 7/2019 | Yang et al. |
| 2019/0308016 A1 | 10/2019 | Wenger et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0023179 A1 | 1/2020 | Bomzon et al. |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0108031 A1 | 4/2020 | Borst et al. |
| 2020/0114141 A1 | 4/2020 | Bomzon et al. |
| 2020/0114142 A1 | 4/2020 | Bomzon et al. |
| 2020/0121728 A1 | 4/2020 | Wardak et al. |
| 2020/0129761 A1 | 4/2020 | Bomzon et al. |
| 2020/0146586 A1 | 5/2020 | Naveh et al. |
| 2020/0155835 A1 | 5/2020 | Wasserman et al. |
| 2020/0171297 A1 | 6/2020 | Kirson et al. |
| 2020/0179512 A1 | 6/2020 | Giladi et al. |
| 2020/0219261 A1 | 7/2020 | Shamir et al. |
| 2020/0269037 A1 | 8/2020 | Hagemann et al. |
| 2020/0269041 A1 | 8/2020 | Zeevi et al. |
| 2020/0269042 A1 | 8/2020 | Giladi et al. |
| 2020/0368525 A1 | 11/2020 | Maag et al. |
| 2021/0031031 A1 | 2/2021 | Wasserman et al. |
| 2021/0038584 A1 | 2/2021 | Voloshin-Sela |
| 2021/0060334 A1 | 3/2021 | Avraham et al. |
| 2021/0069503 A1 | 3/2021 | Tran et al. |
| 2021/0138233 A1 | 5/2021 | Deslauriers |
| 2021/0162228 A1 | 6/2021 | Urman et al. |
| 2021/0177492 A1 | 6/2021 | Travers et al. |
| 2021/0187277 A1 | 6/2021 | Wasserman et al. |
| 2021/0196348 A1 | 7/2021 | Wasserman |
| 2021/0196967 A1 | 7/2021 | Carlson et al. |
| 2021/0199640 A1 | 7/2021 | Patel et al. |
| 2021/0203250 A1* | 7/2021 | Wasserman ........ A61N 1/36002 |
| 2021/0268247 A1 | 9/2021 | Story et al. |
| 2021/0299439 A1 | 9/2021 | Shamir et al. |
| 2021/0299440 A1 | 9/2021 | Deslauriers et al. |
| 2021/0308446 A1 | 10/2021 | Alon et al. |
| 2021/0330950 A1 | 10/2021 | Hagemann et al. |
| 2021/0346694 A1 | 11/2021 | Wasserman et al. |
| 2021/0379362 A1 | 12/2021 | Smith et al. |
| 2021/0408383 A1 | 12/2021 | Kalra et al. |
| 2022/0088403 A1 | 3/2022 | Voloshin-Sela et al. |
| 2022/0095997 A1 | 3/2022 | Wasserman |
| 2022/0096821 A1 | 3/2022 | Kirson et al. |
| 2022/0096829 A1 | 3/2022 | Farber et al. |
| 2022/0118249 A1 | 4/2022 | Bomzon et al. |
| 2022/0161028 A1 | 5/2022 | Giladi et al. |
| 2022/0193435 A1 | 6/2022 | Wasserman et al. |
| 2022/0203111 A1 | 6/2022 | Carlson |
| 2022/0267445 A1 | 8/2022 | Tran et al. |
| 2022/0280787 A1 | 9/2022 | Bomzon et al. |
| 2022/0288395 A1 | 9/2022 | Voloshin-Sela et al. |
| 2022/0313992 A1 | 10/2022 | Wasserman |
| 2022/0323753 A1 | 10/2022 | Voloshin-Sela et al. |
| 2022/0387784 A1 | 12/2022 | Kirson et al. |
| 2022/0395699 A1 | 12/2022 | Doyle |
| 2022/0409893 A1 | 12/2022 | Wasserman et al. |
| 2023/0000384 A1 | 1/2023 | Wasserman et al. |
| 2023/0001197 A1 | 1/2023 | Wasserman et al. |
| 2023/0001221 A1 | 1/2023 | Farber |
| 2023/0009366 A1 | 1/2023 | Voloshin-Sela et al. |
| 2023/0019638 A1 | 1/2023 | Wasserman |
| 2023/0037806 A1 | 2/2023 | Wasserman et al. |
| 2023/0043071 A1 | 2/2023 | Wasserman et al. |
| 2023/0098801 A1 | 3/2023 | Carlson |
| 2023/0141087 A1 | 5/2023 | Giladi et al. |
| 2023/0149708 A1 | 5/2023 | O'Connell et al. |
| 2023/0168242 A1 | 6/2023 | Sarkisian et al. |
| 2023/0188055 A1 | 6/2023 | Wasserman |
| 2023/0191123 A1 | 6/2023 | Wasserman et al. |
| 2023/0201616 A1 | 6/2023 | Carlson |
| 2023/0218912 A1 | 7/2023 | Giladi et al. |
| 2023/0241374 A1 | 8/2023 | Shnaiderman et al. |
| 2023/0248826 A1 | 8/2023 | Giladi et al. |
| 2023/0248969 A1 | 8/2023 | Wasserman et al. |
| 2023/0310848 A1 | 10/2023 | Voloshin-Sela et al. |
| 2023/0310849 A1 | 10/2023 | Wasserman et al. |
| 2023/0310877 A1 | 10/2023 | Giladi |
| 2024/0001111 A1 | 1/2024 | Wasserman et al. |
| 2024/0001115 A1 | 1/2024 | Wasserman et al. |
| 2024/0001117 A1 | 1/2024 | Giladi |
| 2024/0058604 A1 | 2/2024 | Deslauriers et al. |
| 2024/0082592 A1 | 3/2024 | Bomzon et al. |

* cited by examiner

REDUCING ELECTROSENSATION DURING APPLICATION OF ALTERNATING ELECTRIC FIELDS BY ENSURING THAT SUCCESSIVE INCREASES IN AMPLITUDE OCCUR DURING OPPOSITE PHASES OF AN AC WAVEFORM

CROSS REFERENCE TO RELATED APPLICATIONS

This application claims the benefit of U.S. Provisional Application 63/436,034, filed Dec. 29, 2022, which is incorporated herein by reference in its entirety.

BACKGROUND

Tumor Treating Fields (TTFields) therapy is a proven approach for treating tumors using alternating electric fields at frequencies between 50 kHz and 1 MHz (e.g., 150-250 kHz). In the prior art Optune® system, TTFields are delivered to patients via four transducer arrays that are placed on the patient's skin near the tumor. The transducer arrays are arranged in two pairs, with one pair of transducer arrays positioned to the left and right of the tumor, and the other pair of transducer arrays positioned anterior and posterior to the tumor. Each transducer array is connected via a multi-wire cable to an AC signal generator. The AC signal generator (a) sends an AC current through the anterior/posterior (A/P) pair of transducer arrays for 1 second, which induces an electric field with a first direction through the tumor; then (b) sends an AC current through the left/right (L/R) pair of arrays for 1 second, which induces an electric field with a second direction through the tumor; then repeats steps (a) and (b) for the duration of the treatment. Each transducer array includes a plurality (e.g., between 9 and 30) of electrode elements.

Alternating electric fields can also be used to treat medical conditions other than tumors. For example, as described in U.S. Pat. No. 10,967,167 (which is incorporated herein by reference in its entirety), alternating electric fields can be used to increase the permeability of the blood brain barrier so that, e.g., chemotherapy drugs can reach the brain.

When treating a subject using alternating electric fields, higher amplitudes are strongly associated with higher efficacy of treatment. However, as the amplitude of the alternating electric field increases, and/or as the frequency of the alternating electric field decreases (e.g., to the vicinity of 100 kHz), some subjects experience an electrosensation effect. This electrosensation could be, for example, a vibratory sensation, paresthesia, and/or a twitching or contraction sensation of muscle fibers, or a flicker of light in the eyes (phosphene). Electrosensation may discourage some subjects from continuing their treatment using alternating electric fields. Furthermore, electrosensation can limit the amplitude of the alternating electric fields that can comfortably be applied to a given subject, which in turn can limit the efficacy of the treatment.

SUMMARY OF THE INVENTION

One aspect of the invention is directed to a first apparatus that comprises a signal generator and a controller. The signal generator has at least one control input, and the signal generator is configured to generate a first AC output at a frequency between 50 kHz and 1 MHz. The first AC output has an amplitude that depends on a state of the at least one control input. The controller is configured to send a first sequence of control signals to the at least one control input, wherein the first sequence of control signals commands the signal generator to increase an amplitude of the first AC output in a stepwise manner. Each control signal within the first sequence of control signals corresponds to a single step of the stepwise increase in amplitude, and the first sequence of control signals is a sequence of at least 10 control signals. The first sequence of control signals is synchronized with the first AC output such that when a given control signal within the first sequence of control signals commands the signal generator to increase an amplitude of the first AC output while the first AC output has a given polarity, an immediately subsequent control signal within the first sequence of control signals will command the signal generator to increase an amplitude of the first AC output while the first AC output has a polarity that is opposite to the given polarity.

In some embodiments of the first apparatus, the first sequence of control signals is synchronized with the first AC output such that when a given control signal within the first sequence of control signals commands the signal generator to increase an amplitude of the first AC output while the first AC output has a given instantaneous voltage $V_G$, an immediately subsequent control signal within the first sequence of control signals will command the signal generator to increase an amplitude of the first AC output while the first AC output has an instantaneous voltage of $-V_G$, ±20%.

In some embodiments of the first apparatus, the first sequence of control signals is synchronized with the first AC output such that when a given control signal within the first sequence of control signals commands the signal generator to increase an amplitude of the first AC output while the first AC output is operating at a given phase $\phi_G$, an immediately subsequent control signal within the first sequence of control signals will command the signal generator to increase an amplitude of the first AC output while the first AC output is operating at a phase of $\phi_G+180°$, ±10°.

In some embodiments of the first apparatus, the first sequence of control signals is a sequence of at least 20 control signals. In some embodiments of the first apparatus, the first sequence of control signals is a sequence of at least 50 control signals.

In some embodiments of the first apparatus, the controller is further configured to, after sending the first sequence of control signals to the at least one control input, send at least one first control signal to the at least one control input, wherein the at least one first control signal commands the signal generator to hold the amplitude of the first AC output constant for at least half a second. Optionally, in these embodiments, the first AC output has an amplitude greater than 150 V RMS while the amplitude of the first AC output is being held constant.

In some embodiments of the first apparatus, at least half of the steps of the stepwise increase in amplitude have a step height of greater than 2 V. In some embodiments of the first apparatus, the first AC output has a frequency between 75 kHz and 500 kHz.

In some embodiments of the first apparatus, the signal generator is further configured to generate a second AC output at a frequency between 50 kHz and 1 MHZ, and the second AC output has an amplitude that depends on a state of the at least one control input. The controller is further configured to send a second sequence of control signals to the at least one control input, wherein the second sequence of control signals commands the signal generator to increase an amplitude of the second AC output in a stepwise manner. Each control signal within the second sequence of control signals corresponds to a single step of the stepwise increase in amplitude, and the second sequence of control signals is a sequence of at least 10 control signals. The second sequence of control signals is synchronized with the second AC output such that when a given control signal within the second sequence of control signals commands the signal generator to increase an amplitude of the second AC output while the second AC output has a given polarity, an immediately subsequent control signal within the second sequence of control signals will command the signal generator to increase an amplitude of the second AC output while the second AC output has a polarity that is opposite to the given polarity.

Optionally, in the embodiments described in the previous paragraph, the controller may be further configured to, after sending the second sequence of control signals to the at least one control input, send at least one second control signal to the at least one control input. The at least one second control signal commands the signal generator to hold the amplitude of the second AC output constant for at least half a second.

Another aspect of the invention is directed to a first method of increasing an amplitude of an AC voltage. The first method comprises generating an AC voltage, and increasing an amplitude of the generated AC voltage in a stepwise manner. The stepwise increase in amplitude includes at least 10 steps. Each step of the stepwise increase in amplitude is synchronized with the generated AC voltage such that when a given step increases the amplitude of the generated AC voltage while the generated AC voltage has a given polarity, an immediately subsequent step will increase the amplitude of the generated AC voltage while the generated AC voltage has a polarity that is opposite to the given polarity.

In some instances of the first method, each step of the stepwise increase in amplitude is synchronized with the generated AC voltage such that when a given step increases the amplitude of the generated AC voltage while the generated AC voltage has a given instantaneous value XG, an immediately subsequent step will increase the amplitude of the generated AC voltage while the generated AC voltage has an instantaneous value of –XG, ±20%.

In some instances of the first method, each step of the stepwise increase in amplitude is synchronized with the generated AC voltage such that when a given step increases the amplitude of the generated AC voltage while the generated AC voltage is operating at a given phase $\phi_G$, an immediately subsequent step will increase the amplitude of the generated AC voltage while the generated AC voltage is operating at a phase of $\phi$G+180°, ±10°.

In some instances of the first method, the stepwise increase in amplitude includes at least 20 steps. In some instances of the first method, the stepwise increase in amplitude includes at least 50 steps. In some instances of the first method, the generated AC voltage has a frequency between 50 kHz and 1 MHz. In some instances of the first method, the generated AC voltage has a frequency between 75 kHz and 500 kHz.

Another aspect of the invention is directed to a second method of ameliorating electrosensation while applying an electric field to a target region in a living body. The second method comprises applying an alternating electric field having frequency between 50 kHz and 1 MHz to the target region; and increasing an amplitude of the alternating electric field in a stepwise manner. The stepwise increase in amplitude includes at least 10 steps. Each step of the stepwise increase in amplitude is synchronized with the alternating electric field such that when a given step increases the amplitude of the alternating electric field while the alternating electric field has a given polarity, an immediately subsequent step will increase the amplitude of the alternating electric field while the alternating electric field has a polarity that is opposite to the given polarity.

In some instances of the second method, each step of the stepwise increase in amplitude is synchronized with the alternating electric field such that when a given step increases the amplitude of the alternating electric field while the alternating electric field has a given instantaneous value XG, an immediately subsequent step will increase the amplitude of the alternating electric field while the alternating electric field has an instantaneous value of –XG, ±20%.

In some instances of the second method, each step of the stepwise increase in amplitude is synchronized with the alternating electric field such that when a given step increases the amplitude of the alternating electric field while the alternating electric field is operating at a given phase $\phi_G$, an immediately subsequent step will increase the amplitude of the alternating electric field while the alternating electric field is operating at a phase of $\phi_G$+180°, ±10°.

In some instances of the second method, the stepwise increase in amplitude includes at least 20 steps. In some instances of the second method, the stepwise increase in amplitude includes at least 50 steps. In some instances of the second method, the alternating electric field has a frequency between 75 kHz and 500 kHz.

Some instances of the second method further comprise holding the amplitude of the alternating electric field constant for at least half a second after the stepwise increase in amplitude.

BRIEF DESCRIPTION OF THE DRAWINGS

Various embodiments are described in detail below with reference to the accompanying drawings, wherein like reference numerals represent like elements.

DESCRIPTION OF THE PREFERRED
EMBODIMENTS

Figure 1:
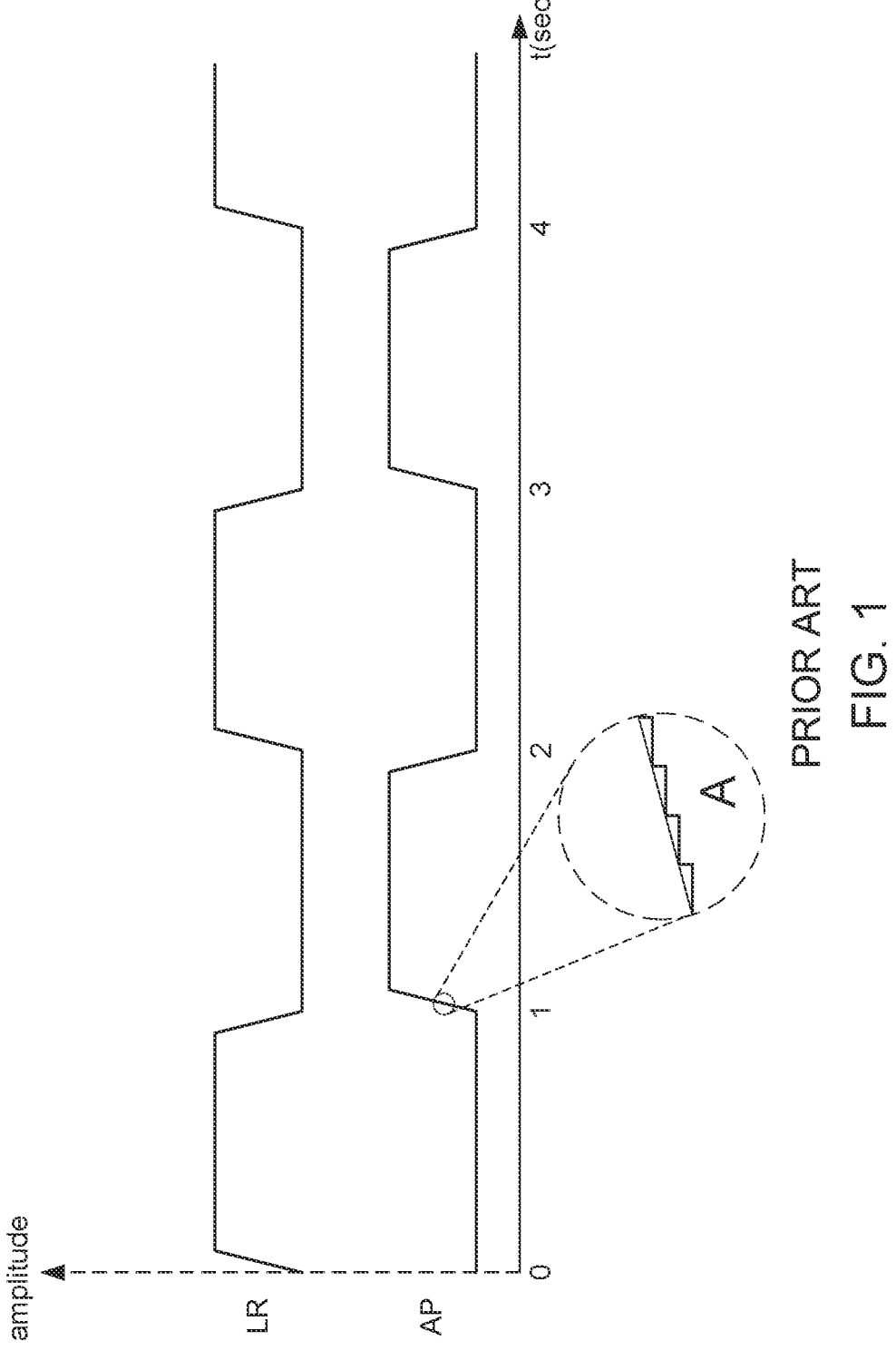
FIG. 1 depicts the AC output amplitudes in two channels of the prior art Optune® system.

FIG. 1 depicts the AC output amplitudes of the L/R channel and the A/P channel in the prior art Optune® system. Notably, when the signal to either the A/P or L/R transducer arrays is turned on during any given one-second interval, the amplitude of the AC voltage does not jump immediately to its peak value. Instead, the amplitude of the AC voltage ramps up from zero to its peak during a first window of time (nominally 100 ms), and then remains at its peak value for a second window of time (nominally 800 ms). Similarly, when the signal is turned off during any given one-second interval, the amplitude of the AC voltage ramps down from its peak to zero during a third window of time (nominally 100 ms).

In the prior art Optune® system, the ramping up and down of the amplitude was implemented by updating a control signal within the AC signal generator at regular 1 ms intervals during the ramp up and ramp down portions of the waveform. Thus, although the main portion of FIG. 1 depicts the ramp-up portion of the waveform as being smooth, zooming in on the waveform reveals that the amplitude actually increases in a stepwise manner, as depicted in inset A of FIG. 1.

The inventors have found that increasing the height of each step (e.g., from 1 V to 2 V) during the ramp-up portion of the waveform makes a much more significant contribution to electrosensation than the increase in overall amplitude (i.e., from 100 VAC RMS to 200 VAC RMS) during the 800 ms middle portion of the waveform.

Without being bound by this theory, electrosensation is believed to originate from interactions between the alternating electric fields and neurons that are positioned near or adjacent to the transducer arrays. More specifically, the inventors believe that one of the main factors that contributes to electrosensation is an accumulation or deficit of ions (e.g., potassium or sodium ions) in neurons. One of the bases for this theory is that electrosensation is typically not observed during the steady-state application of alternating electric fields, even when relatively high AC voltages (e.g., 150-200 V RMS at 100 kHz) are applied to electrodes positioned on a subject's skin. On the other hand, electrosensation has been observed when the voltage applied to those same electrodes ramps up and then ramps back down every 1-2 seconds.

If the accumulation or deficit of ions in neurons is indeed responsible for electrosensation, steady-state application of alternating electric fields should not result in electrosensation because the polarity of the AC signal that is applied to the transducer arrays reverses every half cycle. For if a particular half-cycle of steady-state AC drives a given quantity of ions into a neuron, the very next half-cycle of steady-state AC will drive the same given quantity of ions out of that very same neuron. And under these circumstances, the ions will not accumulate or deplete to a degree that will trigger electrosensation (as long as the AC voltage is not too high e.g., 400-600 V RMS).

Figure 2:
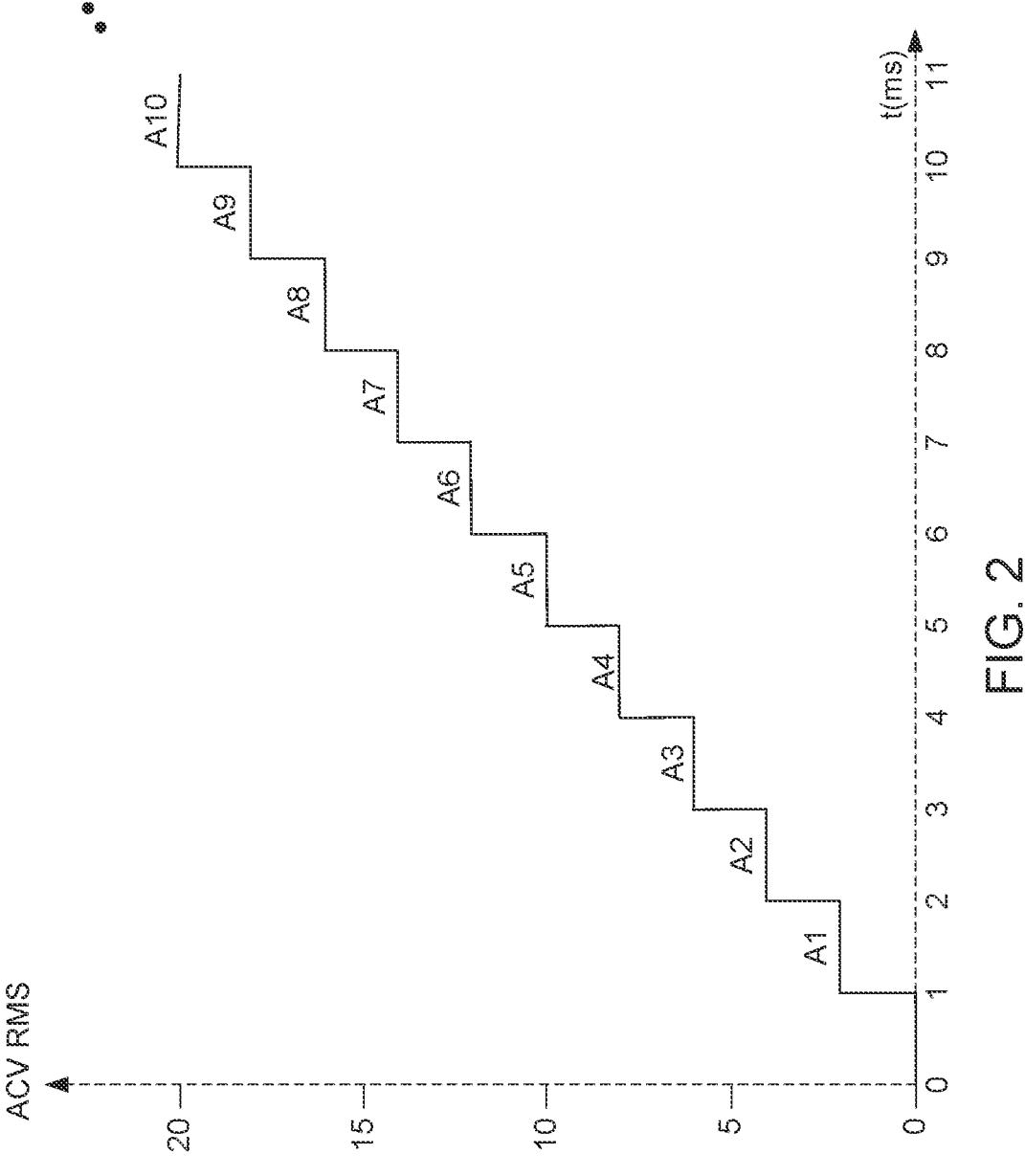
FIG. 2 is a detailed view of the step-to-step transitions in amplitude when the AC voltage ramps up from zero to a peak value.

Let us now analyze the movement of ions if a step height of 2 V is used during the ramp-up portion of the waveform. FIG. 2 depicts the first 10 steps of a ramp-up portion with a 2 V step height and a 1 ms step duration, and this same pattern continues for the duration of the ramp-up portion (e.g., for a total of 100 steps).

Figures 3, 4, 5:
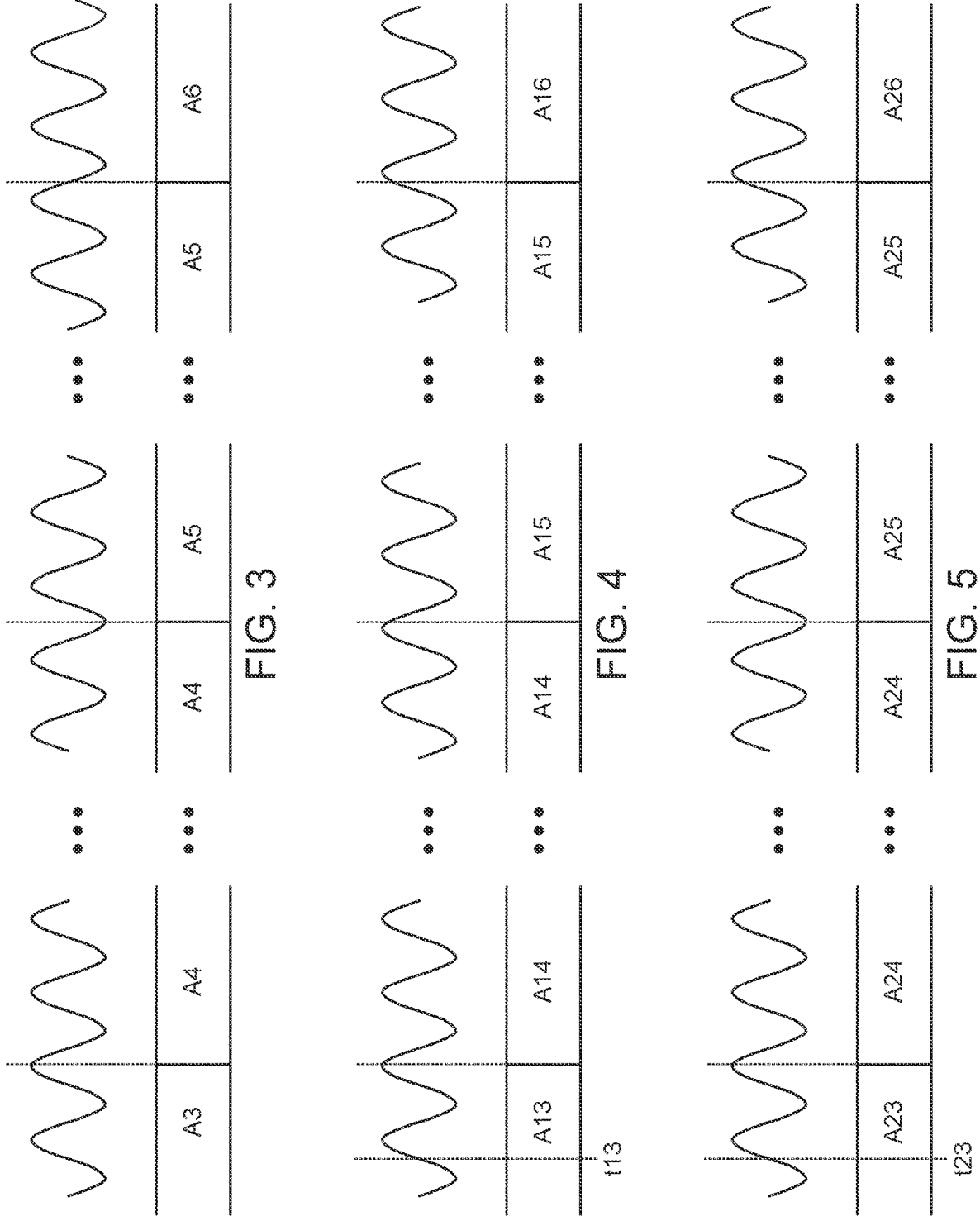
FIG. 3 depicts three examples of how the step-to-step transitions can line up with the instantaneous voltage that is being output by the AC signal generator.
FIG. 4 depicts an example in which successive steps in the ramp-up portion of the waveforms all occur when the output of the AC signal generator is positive.
FIG. 5 depicts an example of how synchronizing the step-to-step transitions with the output of the AC signal generator can ameliorate electrosensation.

FIG. 3 depicts three examples of how the step-to-step transitions can line up with the instantaneous voltage that is being output by the AC signal generator. More specifically, if the output of the AC signal generator is between 0 and 180° at the instant the step-to-step transition occurs (as depicted for the transition from step A3 to A4), the output of the AC signal generator will be positive. If the output of the AC signal generator is between 180 and 360° at the instant the step-to-step transition occurs (as depicted for the transition from step A4 to A5), the output of the AC signal generator will be negative. And if the output of the AC signal generator is exactly at 0° or 180° at the instant the step-tostep transition occurs (as depicted for the transition from step A5 to A6), the output of the AC signal generator will be zero. Note that only three examples are depicted in FIG. 3, and if the timing of the step to step transitions is not synchronized to the output of the AC signal generator (which is the case in the prior art Optune® system), the step-to-step transition could occur anywhere in the sinusoidal cycle (i.e., 0-360°).

If ions are driven into a given neuron when a step-to-step transition occurs when the output of the AC signal generator is positive (as depicted for the transition from step A3 to A4), then ions will be driven out of that same neuron when a step-to-step transition occurs when the output of the AC signal generator is negative (as depicted for the transition from step A4 to A5).

When the height of each step is small enough, one single step will not drive enough ions into the relevant neurons to cause electrosensation. But let us now examine what happens when successive steps in the ramp-up portion of the waveforms all occur when the output of the AC signal generator all have the same polarity, as depicted in FIG. 4. More specifically, in the FIG. 4 example, the transition from step A13 to A14 occurs when the output of the AC signal generator is positive, which means that a first batch of ions will be driven into each of the relevant neurons during that transition. The transition from step A14 to A15 also occurs when the output of the AC signal generator is positive, which means that a second batch of ions will be driven into each of the relevant neurons during that transition. And the transition from step A15 to A16 also occurs when the output of the AC signal generator is positive, which means that a third batch of ions will be driven into each of the relevant neurons during that transition.

If we assume that the number of ions in each of the relevant neurons is at a normal level at time t13, then the transition from step A13 to A14, the transition from step A14 to A15, and the transition from step A14 to A15 will drive three separate batches of ions into each of the relevant neurons (all within a 3 ms window of time). And while not being bound by this theory, the inventors believe that even though driving a single batch of ions into each of the relevant neurons may not be sufficient to cause electrosensation, pushing multiple batches of ions into those same neurons (as the result of successive transitions that all occur during the same polarity of the output of the AC signal generator) in a short interval of time (e.g., <50 ms, <20 ms, <10 ms, or <5 ms) will result in electrosensation.

FIG. 5 is an example of how synchronizing the step-to-step transitions with the output of the AC signal generator can prevent electrosensation, by preventing multiple batches of ions from being driven into the relevant neurons in a short interval of time. We begin by assuming that the number of ions in each of the relevant neurons is at a normal level at time t23. In this FIG. 5 example, the transition from step A23 to A24 occurs when the output of the AC signal generator is positive, which means that a first batch of ions will be driven into each of the relevant neurons during that transition.

But notably, the transition from step A24 to A25 is synchronized with the output of the AC signal generator so that this transition occurs when the output of the AC signal generator is negative. As a result, the second batch of ions will be driven *out of* each of the relevant neurons during that transition. The transition from step A25 to A26 is also synchronized with the output of the AC signal generator so that this transition occurs when the output of the AC signal generator is positive. As a result, the third batch of ions will be driven into each of the relevant neurons during that transition.

Notably, the step-to-step transitions are synchronized with the AC output so that when a given step-to-step transition occurs while the AC output has a given polarity, the very next step-to-step transition will occur while the AC output has the opposite polarity. This will cause the direction of travel of the ions to alternate back and forth between (a) into the neurons and (b) out of the neurons. And this alternation will prevent or at least ameliorate electrosensation by preventing a large quantity of ions from entering (or exiting) each of the relevant neurons within a given window of time.

Optionally, in addition to synchronizing the step-to-step transitions to the alternating polarity of the AC output (to ensure that successive batches of ions travel in opposite directions), some embodiments also try to roughly match the quantity of successive batches of ions. One way to accomplish this is by considering the instantaneous voltage of the AC output. More specifically, the step-to-step transitions can be synchronized with the AC output such that when a given step-to-step transition increases an amplitude of the AC output while the first AC output has a given instantaneous voltage $V_G$, an immediately subsequent step-to-step transition will increase an amplitude of the AC output while the AC output has an instantaneous voltage of $-V_G$, ±20%. This will ensure that the quantity of ions entering a given neuron will match, within 20%, the quantity of ions that exit that neuron.

Another way to roughly match the quantity of successive batches of ions is by considering the phase of the AC output. More specifically, the step-to-step transitions can be synchronized with the AC output such that when a given step-to-step transition increases an amplitude of the AC output while the AC output is operating at a given phase $\phi_G$, an immediately subsequent step-to-step transition will increase an amplitude of the AC output while the first AC output is operating at a phase of $\phi_G+180°$, ±10°. Because the magnitudes of any two points on a sinusoid that are separated by between 170 and 190° will be relatively close (but with opposite signs), this will also ensure that the quantity of ions entering a given neuron will roughly match the quantity of ions that exit that neuron.

Figure 6:
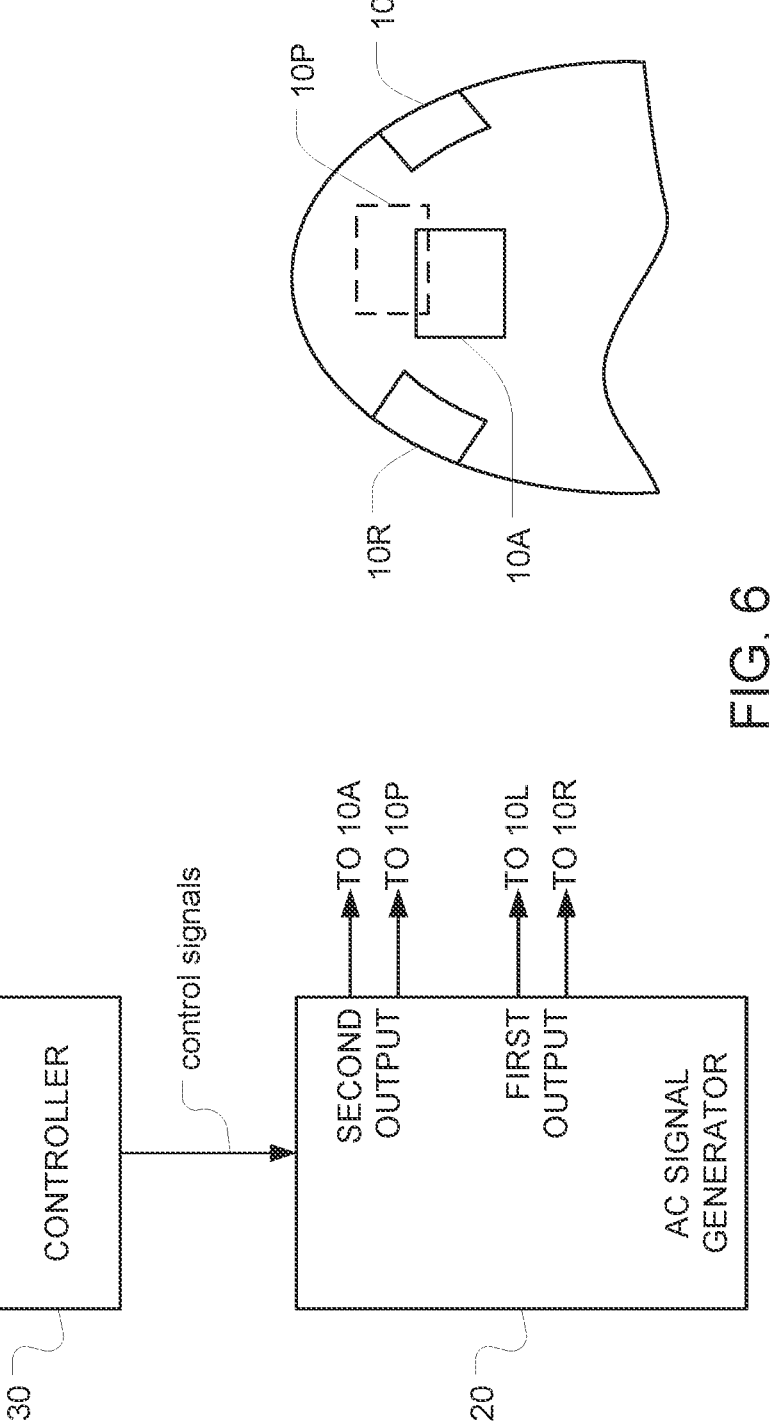
FIG. 6 is a block diagram of a system for driving a set of transducer arrays with AC voltage signals in which the amplitude transitions are synchronized to ameliorate electrosensation.

FIG. 6 is a block diagram of a system for driving a set of transducer arrays with AC voltage signals in which the amplitude transitions are synchronized in the manner depicted in FIG. 5. The system includes an AC signal generator 20 that generates first and second AC outputs at a frequency between 50 kHz and 1 MHz (e.g., 75-500 kHz, 50-300 kHz, or 150-250 kHz). When the system is used to apply TTFields to a person's body, the first AC output is applied across a first pair of transducer arrays 10L and 10R that are positioned to the left and right of the tumor; and the second AC output is applied across a second pair of transducer arrays 10A and 10P that are positioned anterior and posterior to the tumor.

When the AC signal generator 20 applies a voltage between transducer arrays 10L, 10R, an alternating electric field is induced through the target region with field lines that run generally from left to right. And when the AC signal generator 20 applies a voltage between transducer arrays 10A, 10P, an alternating electric field is induced through the target region with field lines that run generally from front to back. The frequency of the alternating electric field will match the frequency of the AC signal generator 20. The electrode elements in the transducer arrays 10 can be capacitively-coupled electrode elements (i.e., electrode elements that include a thin dielectric layer that contacts the subject's body) or conductive electrode elements (i.e., electrode elements that include a conductive surface that contacts the subject's body).

In some embodiments, the voltage generated by the AC signal generator 20 is sufficient to induce an electric field of at least 1 V/cm in at least a portion of the cells. In some embodiments, the voltages generated by the AC signal generator 20 is sufficient to induce an electric field of 1-10 V/cm, 1-20 V/cm, 2-20 V/cm, or 4-20 V/cm in at least a portion of the cells.

Figure 7:
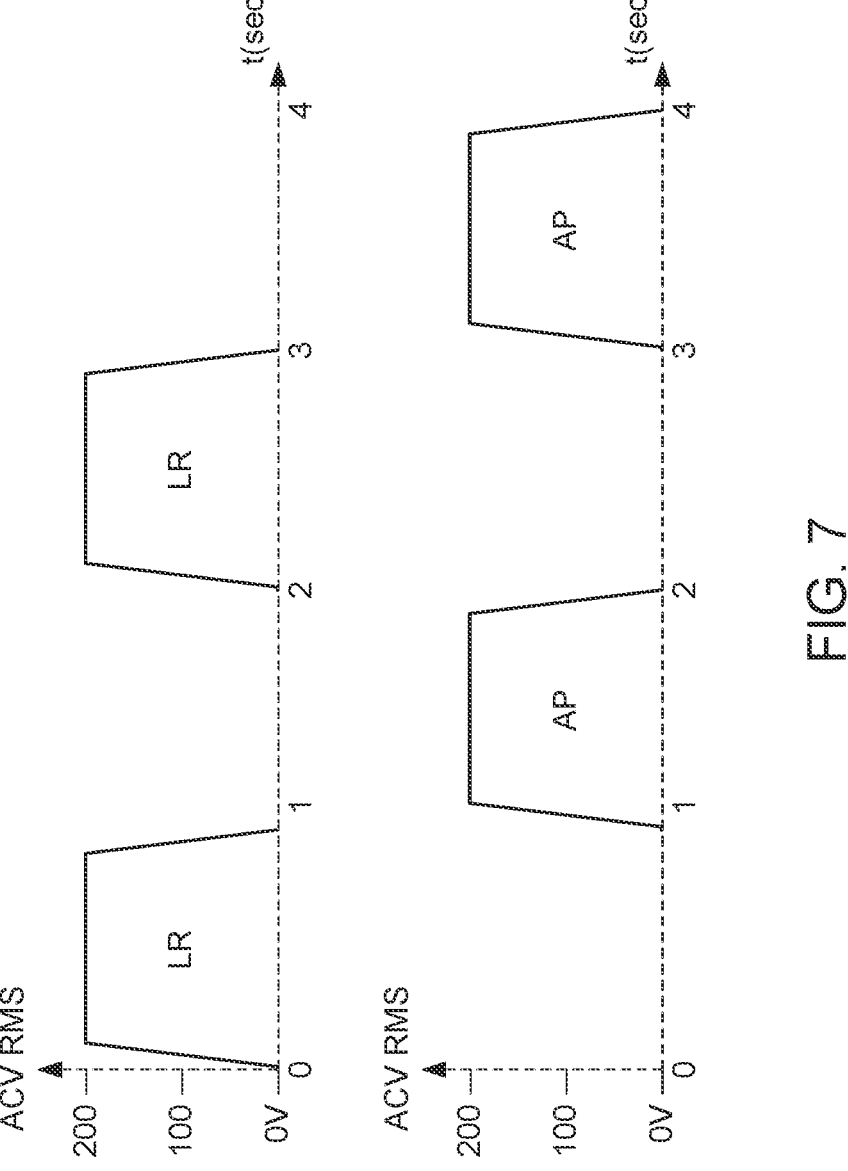
FIG. 7 is a schematic representation of the first and second outputs of the AC signal generator shown in FIG. 6.

As best seen in FIG. 7, (a) the first AC output of the AC signal generator 20 is applied to the L/R transducer arrays 10L, 10R for a period of time; (b) the second AC output of the AC signal generator 20 is applied to the A/P transducer arrays 10A, 10P for a period of time; and the two-step sequence (a) and (b) is repeated for the duration of the treatment. Notably, the way the AC signal generator 20 ramps up its output voltages from zero to their peak in the FIGS. 6/7 embodiment differs from the prior art Optune® system. More specifically, the step-to-step transitions in the amplitude ramp-up are synchronized with the output of the AC signal generator 20 (e.g., as described above in connection with FIG. 5), which can advantageously prevent electrosensation, even when higher voltages (e.g., >150 or >200 VAC RMS) are being output.

The AC signal generator 20 is configured to generate first and second AC outputs with amplitudes that depend on a state of at least one control input at a frequency between 50 kHz and 10 MHz (e.g., 50 kHz-1 MHz, 75-500 kHz, 50-300 kHz, or 150-250 kHz). A controller 30 rapidly sends sequential control signals (e.g., at a rate of 1 control signal per ms) to the at least one control input to control the output amplitude of the AC signal generator 20 to increase the amplitude of the first and second AC outputs in a stepwise manner. Each control signal corresponds to a single step of the stepwise increase in amplitude, and each sequence of control signals is a sequence of at least 10 control signals. In some embodiments, there can be at least 20 control signals or at least 50 control signals.

Note that although FIG. 6 depicts the controller 30 and the AC signal generator 20 as two distinct blocks, those two blocks may be integrated into a single hardware device. In some embodiments, at least half of the steps of the stepwise increase in amplitude have a step height of greater than 2 V. In other embodiments, at least half of the steps of the stepwise increase in amplitude have a step height of >1.5, >1.75, >2.5, >3, >4, or >5 V.

Notably, the sequence of control signals generated by the controller 30 is synchronized with the output of the AC signal generator 20 such that when a given control signal within the sequence of control signals commands the AC signal generator 20 to increase its output amplitude while the AC output has a given polarity, an immediately subsequent control signal will command the AC signal generator 20 to increase its output amplitude while the AC output has a polarity that is opposite to the given polarity (as described above in connection with FIG. 5). And this feature ameliorates electrosensation, as described above in connection with FIG. 5.

After any output has been increased in a stepwise manner as described above, the controller 30 sends at least one control signal to the control input of the AC signal generator 20. These control signal(s) command the AC signal generator 20 to hold the amplitude of the AC output constant for at least half a second (as best seen in FIG. 7). In some embodiments, the AC output has an amplitude greater than 150 V RMS while the amplitude of the AC output is being held constant. In some embodiments, this amplitude can be >150, >175, >200, >225, or >250 V RMS.

The details of the construction of the controller 30 and the nature of the control signals will depend on the design of the AC signal generator 20. In one example, the design of the AC signal generator 20 is similar to the AC signal generator described in U.S. Pat. No. 9,910,453, which is incorporated herein by reference in its entirety. This particular AC signal generator has two output channels (i.e., a first channel for L/R and a second channel for A/P). The instantaneous AC output voltage on either channel depends on the instantaneous output voltage of a DC-DC converter, and the output voltage of that DC-DC converter is controlled by writing control signals to a digital-to-analog converter (DAC), e.g., at a rate of 1 control signal per ms.

The controller 30 in FIG. 6 can therefore implement any desired rate of increase of the first and second outputs of the AC signal generator 20, with any desired pattern, by sequentially sending appropriate control signal to the DAC in the AC signal generator 20. And the required synchronization can be achieved, for example, by having the controller 30 precisely time the exact moment when it issues each control signal. Alternatively, the signal generator 20 can be configured not to act on an incoming command until such time that a particular phase of the AC signal comes around.

In some embodiments (including the embodiment depicted in FIG. 6), the alternating electric field is applied to the subject in two directions in an alternating and repeating sequence (e.g., one second in the L/R direction followed by one second in the A/P direction, repeated for at least one hour). In these embodiments, the signal generator 20 is further configured to generate a second AC output at a frequency between 50 kHz and 10 MHz (e.g., 50 kHz-1 MHZ, 75-500 kHz, 50-300 kHz, or 150-250 kHz), and the second AC output has an amplitude that depends on a state of the at least one control input. In these embodiments, the controller 30 is further configured to send a second sequence of control signals to the at least one control input of the signal generator 20. This sequence of control signals commands the signal generator 20 to increase an amplitude of the second AC output in a stepwise manner. Each control signal within the second sequence of control signals corresponds to a single step of the stepwise increase in amplitude, and the second sequence of control signals is a sequence of at least 10 control signals. And the required synchronization can be achieved, for example, by having the controller 30 precisely time the exact moment when it issues each control signal. Alternatively, the signal generator 20 can be configured not to act on an incoming command until such time that a particular phase of the AC signal comes around.

The second sequence of control signals that is generated by the controller 30 is synchronized with the second AC output such that when a given control signal within the second sequence of control signals commands the signal generator 20 to increase an amplitude of the second AC output while the second AC output has a given polarity, an immediately subsequent control signal within the second sequence of control signals will command the signal generator 20 to increase an amplitude of the second AC output while the second AC output has a polarity that is opposite to the given polarity. This is similar to the situation described above in connection with FIG. 5 for the first AC output.

Returning to FIG. 6, operation of the anterior/posterior channel is similar to the operation for the left/right channel described above in connection with FIG. 5, except that the two channels are activated in an alternating sequence (e.g., at least 1000 times) and are out of phase. When one channel is active, the other channel is off.

A wide variety of alternative designs for the AC signal generator 20 and the controller 30 can be substituted for the example provided above, as long as the controller 30 has the ability to control the AC signal generator 20. For example, if the AC signal generator is designed to respond to an analog control signal, the controller 30 must generate whatever sequence of analog control signals is needed to cause the AC signal generator 20 to output the desired waveforms. In this situation, the controller 30 could be implemented using a microprocessor or microcontroller that is programmed to write appropriate control signals to a digital-to-analog converter, the output of which generates the analog control signals that cause the AC signal generator 20 to generate the desired waveforms. Alternatively, the controller 30 could be implemented using an analog circuit that automatically generates the appropriate sequence of control signals (which are then applied to the control input of the AC signal generator at appropriate times).

In many of the examples described above, the direction of the alternating electric fields was switched between two directions. But in alternative embodiments the direction of the alternating electric fields may be switched between three or more directions (assuming that additional pairs of transducer arrays are provided). For example, the direction of the alternating electric fields may be switched between three directions, each of which is determined by the placement of its own pair of transducer arrays. In other alternative embodiments, the transducer arrays need not be arranged in pairs. See, for example, the transducer array positioning described in U.S. Pat. No. 7,565,205, which is incorporated herein by reference. But regardless of the arrangement of the transducer arrays, increases in amplitude during the ramp-up portion are synchronized with the AC outputs of the AC signal generator 20 e.g., as described above in connection with FIG. 5.

In some anatomic locations, the transducer arrays are not positioned on the subject's skin. Instead, the transducer arrays are implanted into the subject's body (e.g., just beneath the subject's skin) so that application of an AC voltage between the transducer arrays will impose the alternating electric fields in a target region of the subject's body.

Finally, in some anatomic locations, instead of switching the orientation of the alternating electric field back and forth between two or more different directions, an electric field with a constant orientation may be used. Embodiments for use with these locations are similar to the FIG. 6 embodiment, except that the AC signal generator 20 has only a single output (e.g., only the L/R output). In these embodiments, the AC voltage generator is configured to, when initially switched on, ramp its voltage up as described above in connection with FIG. 5, and then either leave its output voltage at a fixed level for the duration of the treatment, or switch the single output on and off repeatedly (e.g., on for 1-10 s and off for 0.1-10 s). In the latter situation, each time the AC voltage generator switches back on, it ramps its voltage up as described above in connection with FIG. 5.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of ameliorating electrosensation while applying an electric field to a target region in a living body, the method comprising:

applying an alternating electric field having frequency between 50 kHz and 1 MHz to the target region; and increasing an amplitude of the alternating electric field in a stepwise manner, wherein the stepwise increase in amplitude includes at least 10 steps, wherein each step of the stepwise increase in amplitude is synchronized with the alternating electric field such that when a given step increases the amplitude of the alternating electric field while the alternating electric field has a given polarity, an immediately subsequent step will increase the amplitude of the alternating electric field while the alternating electric field has a polarity that is opposite to the given polarity.

2. The method of claim 1, wherein each step of the stepwise increase in amplitude is synchronized with the alternating electric field such that when a given step increases the amplitude of the alternating electric field while the alternating electric field has a given instantaneous value $X_G$, an immediately subsequent step will increase the amplitude of the alternating electric field while the alternating electric field has an instantaneous value of $-X_G$, $\pm20\%$.

3. The method of claim 1, wherein each step of the stepwise increase in amplitude is synchronized with the alternating electric field such that when a given step increases the amplitude of the alternating electric field while the alternating electric field is operating at a given phase $\phi_G$, an immediately subsequent step will increase the amplitude of the alternating electric field while the alternating electric field is operating at a phase of $\phi_G+180°$, $\pm10°$.

4. The method of claim 1, wherein the alternating electric field has a frequency between 75 kHz and 500 kHz.

* * * * *